(12) United States Patent
Steinberg et al.

(10) Patent No.: US 10,363,014 B1
(45) Date of Patent: Jul. 30, 2019

(54) STEERABLE ULTRASOUND ATTACHMENT FOR ENDOSCOPE

(71) Applicants: Stephen E. Steinberg, Boca Raton, FL (US); Scott Sutherland Corbett, III, Portland, OR (US)

(72) Inventors: Stephen E. Steinberg, Boca Raton, FL (US); Scott Sutherland Corbett, III, Portland, OR (US)

(73) Assignee: ENDOSOUND, LLC, Boca Raton, FL (US)

( * ) Notice: Subject to any disclaimer, the term of this patent is extended or adjusted under 35 U.S.C. 154(b) by 0 days.

(21) Appl. No.: 15/951,347

(22) Filed: Apr. 12, 2018

(51) Int. Cl.
*A61B 8/12* (2006.01)
*A61B 8/00* (2006.01)
*A61B 1/00* (2006.01)
*A61B 10/04* (2006.01)
*A61B 17/00* (2006.01)

(52) U.S. Cl.
CPC ........ *A61B 8/4444* (2013.01); *A61B 1/00133* (2013.01); *A61B 8/12* (2013.01); *A61B 10/04* (2013.01); *A61B 2010/045* (2013.01); *A61B 2017/0034* (2013.01)

(58) Field of Classification Search
None
See application file for complete search history.

(56) References Cited

U.S. PATENT DOCUMENTS

| 4,802,487 | A | 2/1989 | Martin et al. |
| 6,099,464 | A | 8/2000 | Shimizu et al. |
| 6,409,666 | B1 | 6/2002 | Ito |
| 6,461,304 | B1 | 10/2002 | Tanaka et al. |
| 7,771,349 | B2 | 8/2010 | Kohno |
| 8,303,508 | B2 | 11/2012 | Wakabayashi et al. |
| 8,657,749 | B2 | 2/2014 | Sato |
| 8,708,931 | B2 | 4/2014 | Takeuchi et al. |
| 8,827,922 | B2 | 9/2014 | Aoki et al. |
| 8,870,778 | B2 | 10/2014 | Tsutaki et al. |
| 8,900,152 | B2 | 12/2014 | Ogawa et al. |

(Continued)

OTHER PUBLICATIONS

Manta, Rafaele et al., Clinical Clip: EUS Fine Needle Aspiration Procedure, Endoscopy Unit Nuovo Ospedale Civile Sant'Agostino Estense, Baggiovara, Modena, Italy, Cook Endoscopy 2009.

*Primary Examiner* — Patricia J Park
(74) *Attorney, Agent, or Firm* — Timothy E. Siegel Patent Law, PLLC; Timothy E. Siegel

(57) ABSTRACT

An ultrasound assembly adapted to be attached to an endoscope includes a multiconductor electrical connector and a first multiconductor cable connected to the connector. An endoscope attachment element, attached to the multiconductor cable is sized to attach to the distal end of the endoscope and a resiliently deformable neck is connected and extends in a distal manner from the distal end of the first multiconductor cable, and has a distal end. A second multiconductor cable has a proximal end connected to the distal end of the first multiconductor cable. Further, an ultrasound transducer head includes a protective covering, supported by the distal end of the neck, and an ultrasound transducer, inside the protective covering and electrically connected to the distal end of the second multiconductor cable. Finally, a tension member is connected to the ultrasound transducer head and is long enough to extend along the length of the target endoscope.

22 Claims, 4 Drawing Sheets

(56) References Cited

U.S. PATENT DOCUMENTS

| | | | |
|---|---|---|---|
| 9,332,961 B2 | 5/2016 | Ogawa | |
| 2001/0031923 A1* | 10/2001 | Seward | A61B 5/6826 |
| | | | 600/459 |
| 2009/0093725 A1* | 4/2009 | Sato | A61B 1/0051 |
| | | | 600/462 |
| 2014/0114195 A1 | 4/2014 | Inui et al. | |
| 2015/0087994 A1 | 3/2015 | Matsuno et al. | |

* cited by examiner

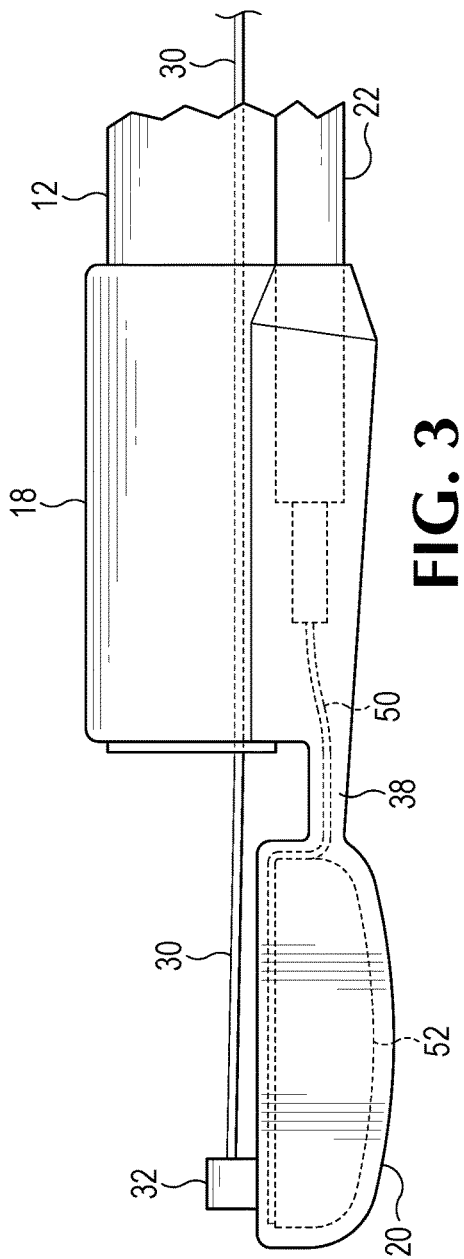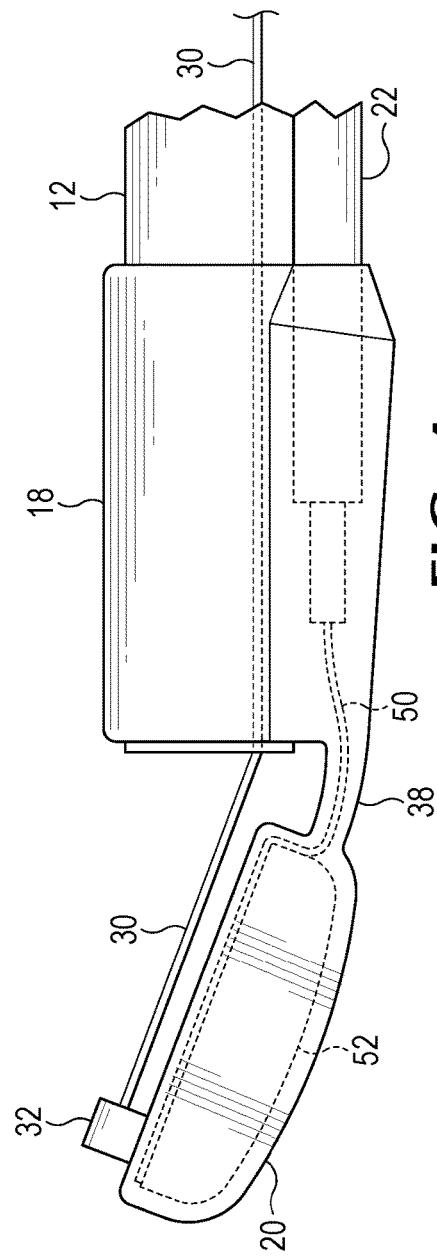

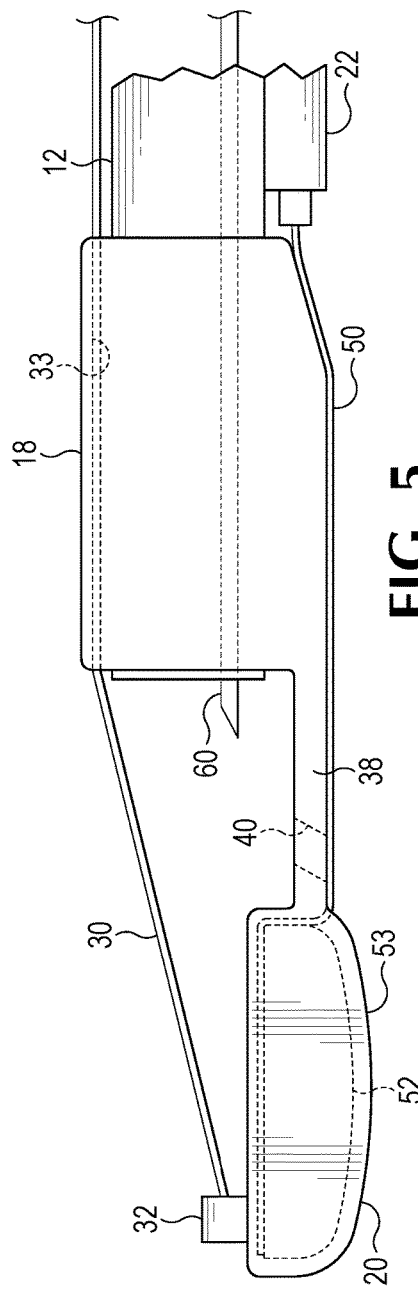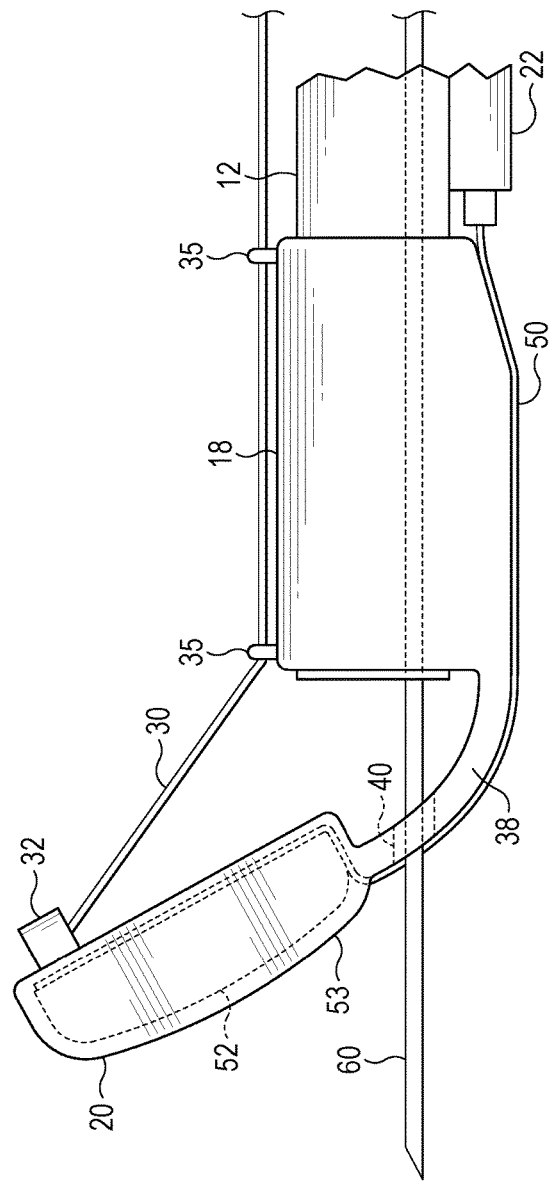

STEERABLE ULTRASOUND ATTACHMENT FOR ENDOSCOPE

BACKGROUND

Endoscopic ultrasound has undergone a rapid pace of development, now being used for the diagnosis and treatment of a wide variety of medical problems. As an endoscope can reach a location in the intestinal tract, closer than any skin surface, there is an opportunity to image from a closer location, and to obtain a tissue sample, using a biopsy needle and implement a variety of treatments. But due to an expense of greater than $200,000 for a complete system, endoscopic ultrasound systems are generally restricted to major hospitals. Endoscopes, however, are used in physicians' offices, most outpatient surgery centers and virtually all hospitals.

BRIEF DESCRIPTION OF THE DRAWINGS

Exemplary embodiments are illustrated in referenced drawings. It is intended that the embodiments and figures disclosed herein are to be considered illustrative rather than restrictive.

FIG. 3 is a side view of the distal end of the assembly of FIG. 1, in a first position.

FIG. 4 is a side view of the distal end of the assembly of FIG. 1, in a second position.

FIG. 5 is a side view of the distal end of an alternative embodiment of an imaging assembly.

FIG. 6 is a side view of another alternative embodiment of an imaging assembly.

SUMMARY

Figure 1:
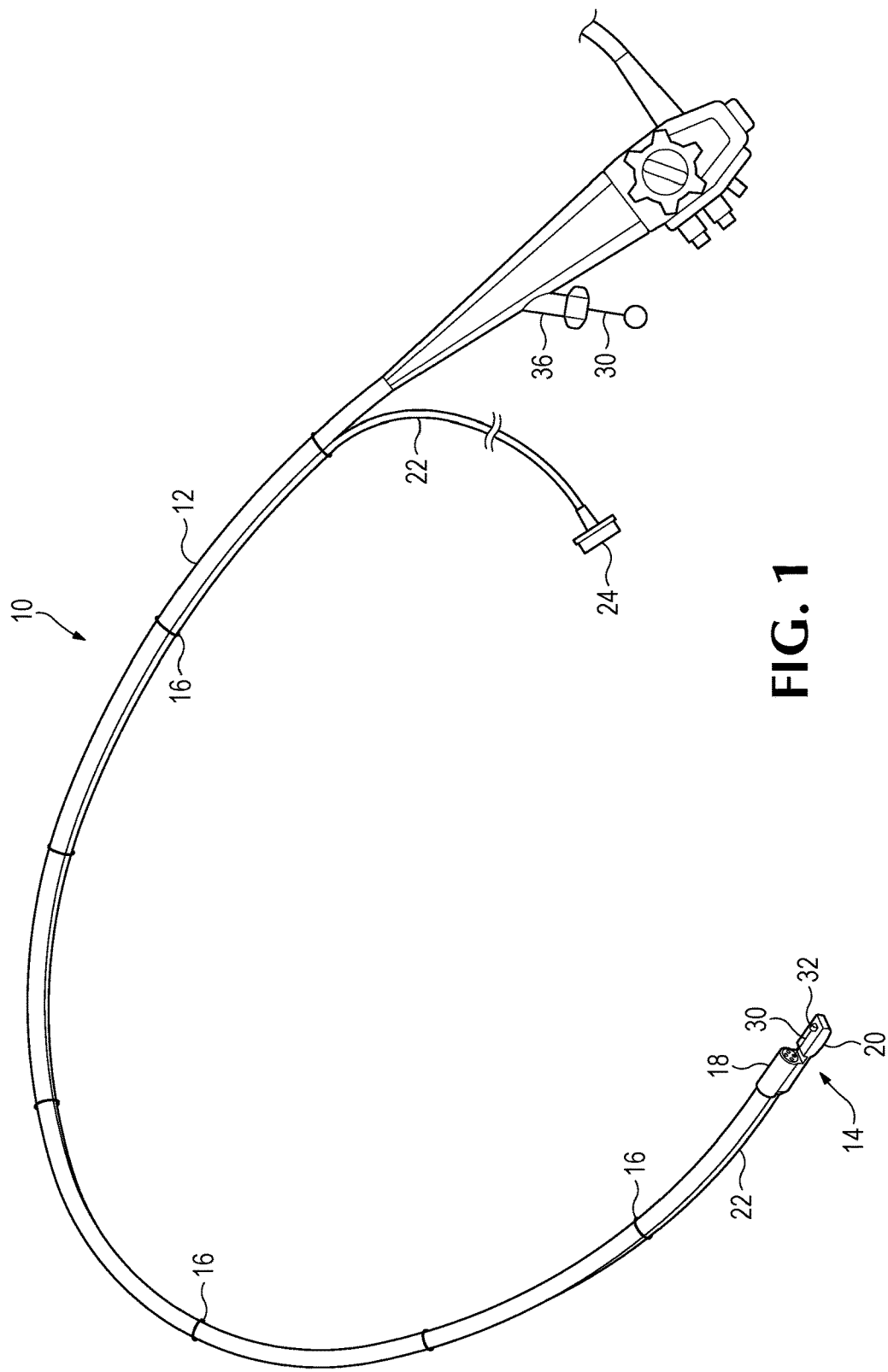
FIG. 1 is an isometric view of an imaging assembly having an endoscope and an ultrasound imaging assembly added on, according to a preferred embodiment of the present invention.

In a first separate aspect, the present invention may take the form of a method of adding elements to an endoscope, to create an ultrasound capable endoscope, which has a distal end and an elongate body defining one or more lumens. The method uses an ultrasound assembly that has a multiconductor electrical connector; a first multiconductor cable, including a multiplicity of coaxial cables, connected to the multiconductor electrical connector, and having a distal end; an endoscope attachment element, attached to the first multiconductor cable, and sized to attach to the distal end of the endoscope; a neck, connected and extending in a distal manner from the distal end of the first multiconductor cable, and having a distal end, the neck being resiliently deformable; a second multiconductor cable, having a proximal end connected to the distal end of the first multiconductor cable, and having a distal end; an ultrasound transducer head, including a protective covering, supported by the distal end of the neck, and an ultrasound transducer, inside the protective covering and electrically connected to the distal end of the second multiconductor cable; and a tension member, connected to the ultrasound transducer head, and extending to the proximal end of the endoscope; The ultrasound attachment element is attached to the distal end of the endoscope, and the tension member is arranged so that it extends from a proximal point of the endoscope to the transducer head. Accordingly, the ultrasound transducer head can be introduced into a patient body cavity, with the endoscope, and may be angle adjusted by the tension member thereby adjusting position of the ultrasound transducer head and may communicate with an imaging station by means of the first and second multiconductor cables.

In a second separate aspect, the present invention may take the form of a method of adjusting the viewing angle of an imaging assembly having an endoscope and an added ultrasound imaging array. The array is part of an ultrasound assembly that includes a multiconductor electrical connector; a first multiconductor cable, including a multiplicity of coaxial cables, connected to the multiconductor electrical connector, and having a distal end; an endoscope attachment element, attached to the first multiconductor cable, and also attached to the distal end of the endoscope; a neck, connected and extending in a distal manner from the distal end of the first multiconductor cable, and having a distal end, the neck being resiliently deformable; a second multiconductor cable, having a proximal end connected to the distal end of the first multiconductor cable, and having a distal end; an ultrasound transducer head, including a protective covering, supported by the distal end of the neck, and an ultrasound transducer, inside the protective covering and electrically connected to the distal end of the second multiconductor cable; and a tension member, connected to the ultrasound transducer head, and extending to the proximal end of the endoscope so that a free end of the tension member is accessible to a human operator. The method begins, once the multiconductor electrical connector has been connected to an ultrasound imaging station and the ultrasound transducer head has been introduced into a cavity of a patient, with the endoscope and includes pulling on the free end the tension member to cause the ultrasound transducer head to move from a position that is aligned to the distal end of the endoscope to a position bent at an obtuse angle relative to the distal end of the endoscope and permitting the free end to retract toward the lumen, thereby permitting the ultrasound transducer head to move back toward the position aligned to the distal end of the endoscope, thereby scanning a portion of the patient's internal organs.

In a third separate aspect, the present invention may take the form of an ultrasound assembly adapted to be attached to a target endoscope includes a multiconductor electrical connector and a first multiconductor cable, including a multiplicity of coaxial cables, connected to the connector, and has a distal end. An endoscope attachment element, attached to the multiconductor cable is sized to attach to the distal end of the target endoscope and a neck is connected and extends in a distal manner from the distal end of the first multiconductor cable, and has a distal end, the neck being resiliently deformable. A second multiconductor cable has a proximal end connected to the distal end of the first multiconductor cable and has a distal end. Further, an ultrasound transducer head includes a protective covering, supported by the distal end of the neck, and an ultrasound transducer, inside the protective covering and electrically connected to the distal end of the second multiconductor cable. Finally, a tension member is connected to the ultrasound transducer head and is long enough to extend along the length of the target endoscope.

In a fourth separate aspect, the present invention may take the form of an ultrasound capable endoscope, including an endoscope, having a distal end and an elongated body defining one or more lumens and an ultrasound assembly removably connected to the endoscope. The ultrasound assembly has a multiconductor electrical connector; a first multiconductor cable, including a multiplicity of coaxial cables, connected to the multiconductor electrical connector, and having a distal end; an endoscope attachment element, attached to the first multiconductor cable, and sized to attach to the distal end of the endoscope; a neck, connected and extending in a distal manner from the distal end of the first multiconductor cable, and having a distal end, the neck being resiliently deformable; a second multiconductor cable, having a proximal end connected to the distal end of the first multiconductor cable, and having a distal end; an ultrasound transducer head, including a protective covering, supported by the distal end of the neck, and an ultrasound transducer, inside the protective covering and electrically connected to the distal end of the second multiconductor cable; and a tension member, connected to the ultrasound transducer head, and extending to the proximal end of the endoscope. The tension member extends from a proximal point of the endoscope to the transducer head. Accordingly, the ultrasound transducer head can be introduced into a patient body cavity, with the endoscope, and may be angle adjusted by the tension member thereby adjusting position of the ultrasound transducer head and may communicate with a station by means of the first and second multiconductor cables.

DETAILED DESCRIPTION OF THE
PREFERRED EMBODIMENTS

Definition

As used in this application, the term "endoscope" refers to an illuminated optical, typically slender and tubular instrument used to look deep into the body and used in procedure referred to as "endoscopy". This term encompasses, but is not limited to upper endoscopes, colonoscopes and bronchoscopes, as well as devices referenced simply as "endoscopes".

Description

In a first preferred embodiment, an imaging assembly 10 includes an endoscope 12 and an ultrasound assembly 14 that has been attached to endoscope 12 by means of retaining element 18, integral to ultrasound assembly 14. Assembly 14 also includes an ultrasound imaging (also referred to as "transducer") head 20 that is electrically connected to a multiconductor cable 22 by way of a flex circuit 50 (which is also a form of a multiconductor cable), that includes a set of parallel electrical leads, which may be traces. Cable 22, which has a multiplicity of coaxial cables extending therethrough terminates in a connector 24, adapted to connect to an imaging station. Elements 16, which may be rubber bands, or some other form of elastic bands or clips, help to retain cable 22, to the side of endoscope 12. A tension member 30, such as a wire (which may also have some compressive strength) is attached to a bump 32 on ultrasound imaging head 20 and extends through a lumen 34 (FIG. 2) to emerge outside of a port 36 on the proximal end of endoscope 12, to be manipulated. In embodiments, tension member 30, does not extend through lumen 34, but extends along the side of endoscope 12, and in embodiments is retained by elements 16, which are modified from the simple shapes shown in FIG. 1, to include eyelets, to create a guide path for tension member 30. In one embodiment, tension member 30 is connected to controls on the proximal end of endoscope 12, to facilitate manipulation. In embodiments, these controls may take the form of a spool, that can be easily let out, or drawn in. Endoscope 12 also is equipped with intrinsic controls for deflecting the tip of the insertion tube, to facilitate introduction to a site of interest.

Figure 2:
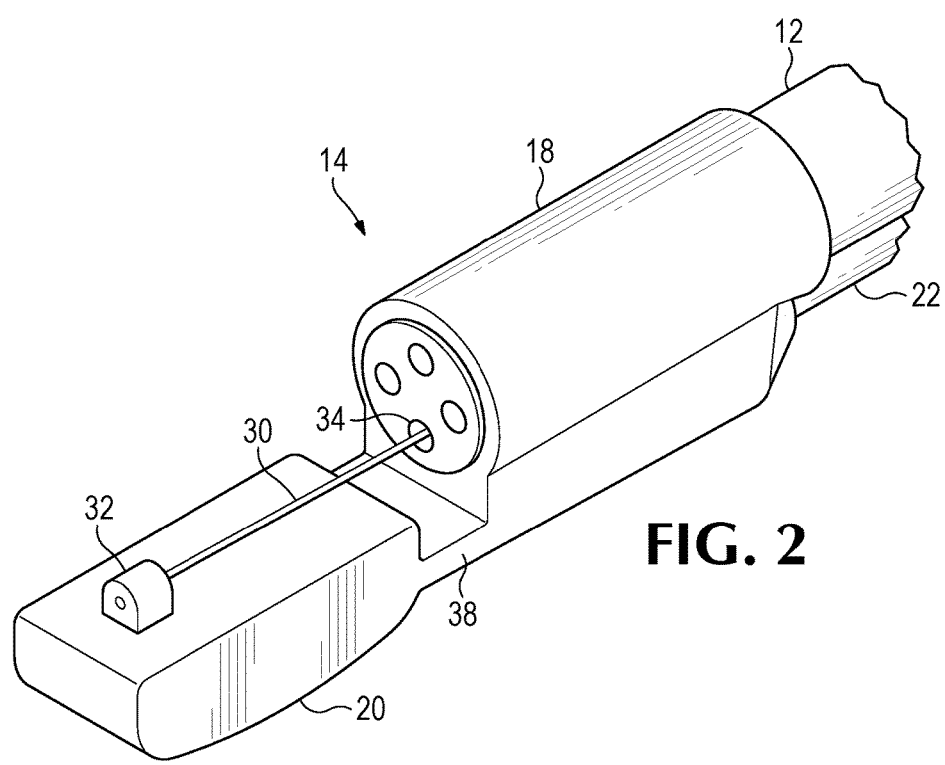
FIG. 2 is an isometric view of the distal end of the assembly of FIG. 1.

In an alternative embodiment, tension member 30 is replaced by a tension member extending along the exterior of the endoscope, to a fixation point on the end of the endoscope. A physician may exert traction on tension member 30 in any one of a variety of ways, to cause ultrasound imaging head 20 to bend back toward retaining element 18, as permitted by a resiliently flexible neck 38 (FIG. 2). In one method a rotatable element is used to draw in tension member 30.

In preferred embodiment endoscope 12 includes an element at its distal end to guide the alignment of the retaining element 18. For example, endoscope 12 many include a groove at its distal end, into which a key element on retaining element 18 engages. In another embodiment, an orientation guide includes a peg that fits into the lumen 34 and is used to guide the correct orientation of retaining element 18. In one embodiment, assembly 14 is made for intended disposal, after a single use, and is used in this manner. In another embodiment, assembly 14 is constructed so as to be prepared and/or cleaned appropriately for reuse, after use, and then reused.

Referring to FIGS. 3 and 4, a flex circuit 50, which passes through the flexible neck 38, electrically connects imaging head 20 to cable 22. Flex circuit 50 has an electrical lead for each transducer element in an ultrasound element array 52, resident in the ultrasound imaging head 20, to drive ultrasound element array 52 and relay signals from it. Array 52 is covered with a protective coating 53.

In a preferred embodiment a biopsy needle 60 (FIGS. 5 and 6), which forms the sharpened, distal portion of a long, flexible, hollow-core wire. This wire is sheathed in a flexible conduit (not shown), thin enough to extend through the lumen 34 and protecting endoscope 12 from being damaged by needle 60. Once the conduit reaches the distal end of endoscope 12, it may be pushed out to extend from lumen 34, and provide further guidance for needle 60, which is pushed out of the conduit at a point distal to the end of endoscope 12. Alternatively, the conduit may be pushed roughly to the end of lumen 34, with the needle pushed out of the conduit at that point.

Referring to FIG. 5, in an alternative preferred embodiment tension member 30 extends through a channel 33 in retaining element 18 to reach bump 32. This figure also shows a needle 60 that has been pushed through a lumen of the endoscope 12 and is emerging from the distal end of the lumen. An aperture 40 is defined in neck 38, corresponding to an aperture in flex circuit 50, aligned with aperture 40, FIG. 6 shows an embodiment that is similar to that of FIG. 5, but instead with tension member 30 extending through a pair of eyelets 35, supported on the retaining element 18. As well as showing a slightly different embodiment, FIG. 6 also shows imaging head 20 retracted and needle 60 extending through aperture 40, as it would be in order to take a biopsy. Notably, in this position the needle would be within the field of view of ultrasound array 52. In embodiments, tension member 30 can pull head 20 into an obtuse angle, relative to the distal end of the endoscope 12. Generally, aperture 40 is in the shape of a long oval, so that the needle 60 can pass through it over a long range of degree of bending of neck 38. In another preferred embodiment, the flexible conduit is extended distally from lumen 34 into a v-shaped indentation (not shown) on surface of flexible neck 38, aligning the sheath so that the needle 60 is aligned to pass through aperture 40.

To use imaging assembly 10, ultrasound assembly 14 is attached to endoscope 12 by means of retaining element 18. In an alternative embodiment, rubber bands or clips 16 retain ultrasound cable 22 to the side of endoscope 12. Imaging head 20 is then delivered to an area of interest, by means of standard endoscope introduction techniques. Imaging head 20 may then be moved to gain imagery of the area of interest by dedicated controls which control the ultrasound imaging head 20 deflection. If there appears to be a finding to be sampled, needle 60 may be introduced through an endoscope lumen and through aperture 40 and used to take a biopsy, inject a drug, or otherwise effect a medical procedure. Finally, needle 60 is retracted through the lumen of endoscope 12 and the endoscope is retrieved from the patient's body. In other embodiments, needle 60 is not included and an assembly that is similar to imaging assembly 10 but without needle 60 and related elements, is used for imaging alone.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of adding elements to an endoscope, to create an ultrasound capable endoscope, comprising:
   a. providing an endoscope, having a distal end and an elongate body defining one or more lumens;
   b. providing an ultrasound assembly that includes:
      i. a multiconductor electrical connector,
      ii. a first multiconductor cable, including a multiplicity of coaxial cables, connected to said multiconductor electrical connector, and having a distal end;
      iii. an endoscope attachment element, attached to said first multiconductor cable, and sized to attach to said distal end of said endoscope;
      iv. a neck, connected and extending in a distal manner from said distal end of said first multiconductor cable, and having a distal end, said neck being resiliently deformable;
      v. a second multiconductor cable, having a proximal end connected to said distal end of said first multiconductor cable, and having a distal end;
      vi. an ultrasound transducer head, including a protective covering, supported by said distal end of said neck, and an ultrasound transducer, inside said protective covering and electrically connected to said distal end of said second multiconductor cable; and
      vii. a tension member, connected to said ultrasound transducer head, and extending to said proximal end of said endoscope;
   c. attaching said endoscope attachment element to said distal end of said endoscope and arranging said tension member so that it extends from a proximal point of said endoscope to said transducer head;
   d. whereby said ultrasound transducer head can be introduced into a patient body cavity, with said endoscope, and may be angle adjusted by said tension member by pulling on said tension member to bend said neck thereby adjusting position of said ultrasound transducer head, and may communicate with an imaging station by means of said first and second multiconductor cables, thereby permitting a user to more accurately aim the imaging head at a feature of interest; and
   e. further wherein said neck defines an aperture, permitting a needle to be extended from a lumen of said endoscope, through said aperture, to perform a medical procedure, when said neck is flexed by said tension member.

2. The method of claim 1, wherein said second multiconductor cable extends through said neck.

3. The method of claim 1, further including pushing a needle through a lumen of said endoscope, to position it to be pushed out of said endoscope, to perform a medical procedure.

4. The method of claim 1, further including providing attachment elements and using said attachment elements to attach said first multiconductor cable to said endoscope.

5. The method of claim 4, wherein said attachment elements are elastic bands.

6. The method of claim 1, wherein said arranging said tension member is accomplished by threading said tension member through a lumen of said endoscope.

7. The method of claim 1, wherein said arranging said tension member is accomplished by constraining said tension member on said endoscope exterior.

8. The method of claim 1, wherein said endoscope has a key element on its distal end and said ultrasound assembly includes a cooperative element on said endoscope attachment element, whereby a user is facilitated in attaching said endoscope attachment element at a correct orientation relative to said key element.

9. The method of claim 1, wherein ultrasound assembly includes an orientation guide on said endoscope attachment element, to guide a user in attaching said endoscope attachment element in a correct orientation relative to a lumen of said endoscope.

10. The method of claim 1, further including:
    a. providing a key unit, having a peg adapted to fit into a lumen of said endoscope, and further being shaped to fit onto said distal end of said endoscope when said peg is in said lumen, in a single orientation only;
    b. attaching said key unit at said distal end by pushing said peg into said lumen;
    c. using said key unit to guide attachment of said endoscope attachment element of said ultrasound assembly.

11. The method of claim 1, wherein said ultrasound assembly is an unused ultrasound assembly and wherein said ultrasound assembly is disposed, after being used a single time.

12. The method of claim 1, wherein said ultrasound capable endoscope is used in a medical procedure after said ultrasound capable endoscope has been created, and wherein said ultrasound assembly is reused, after said use.

13. The method of claim 1, wherein said aperture is an elongate oval, and wherein said needle can pass through said aperture when said neck is bent in any degree selected from a long range of degree of bending.

14. The method of claim 1, wherein when said neck is flexed by said tension member and said needle is passed through said aperture, said needle is visible in a field of view of said ultrasound transducer, thereby permitting a user to more accurately guide said needle.

15. The method of claim 7, wherein said tension is constrained on said endoscope exterior by providing eyelets on said attachment elements and threading said tension member through said eyelets.

16. A method of adding elements to an endoscope, to create an ultrasound capable endoscope, comprising:
    a. providing an endoscope, having a distal end and an elongate body defining one or more lumens;
    b. providing an ultrasound assembly that includes:
       i. a multiconductor electrical connector,
       ii. a deformable neck, having a proximal end and a distal end;

iii. an ultrasound transducer head supported by said distal end of said neck, and including an ultrasound transducer; and iv. a tension member, connected to said ultrasound transducer head, and extending to said proximal end of said endoscope;

v. a set of electrically conductive pathways, extending from said ultrasound transducer to said multiconductor electrical connector; and c. attaching said ultrasound assembly to said endoscope, so that said ultrasound assembly extends along said elongate body of said endoscope, and so that said ultrasound transducer head is held by said neck at a position distal to said distal end of said endoscope, and arranging said tension member so that it extends from a proximal point of said endoscope to said transducer head;

d. whereby said ultrasound transducer head can be introduced into a patient body cavity, with said endoscope, and may be angle adjusted by said tension member by pulling on said tension member to bend said neck thereby adjusting position of said ultrasound transducer head, and may communicate with an imaging station by means of said electrically conductive pathways, thereby permitting a user to more accurately aim the imaging head at a feature of interest; and e. further wherein said neck defines an aperture, permitting a needle to be extended from a lumen of said endoscope, through said aperture, to perform a medical procedure, when said neck is flexed by said tension member.

17. The method of claim 16, wherein said electrically conductive pathways are made up of a first multiconductor electrical cable, connected to said multiconductor electrical connector, and having a distal end and a second multiconductor cable, having a proximal end connected to said distal end of said first multiconductor cable, and having a distal end connected to said ultrasound transducer.

18. The method of claim 17, wherein said first multiconductor cable includes a multiplicity of coaxial cables.

19. The method of claim 17 wherein said second multiconductor cable is a flex circuit.

20. The method of claim 17, wherein said ultrasound assembly further includes an attachment element, and said ultrasound assembly is attached to said endoscope, at least in part, by attaching said attachment element to said distal end of said endoscope.

21. The method of claim 20, wherein said attachment element is a clip sized and shaped to engage to said distal end of said endoscope.

22. The method of claim 16, wherein said neck is resiliently deformable.

* * * * *